United States Patent
Chen

(10) Patent No.: US 7,709,587 B2
(45) Date of Patent: May 4, 2010

(54) ERASER COMPOSITION FOR DE-FLAKES

(76) Inventor: Yin-Tsan Chen, No. 280, Ping Hsi Rd., Shalu Chen, Taichung Hsien (TW)

( * ) Notice: Subject to any disclaimer, the term of this patent is extended or adjusted under 35 U.S.C. 154(b) by 698 days.

(21) Appl. No.: 11/561,892

(22) Filed: Nov. 21, 2006

(65) Prior Publication Data

US 2008/0118459 A1    May 22, 2008

(51) Int. Cl.
*C08F 12/08*    (2006.01)
*C08K 5/00*    (2006.01)

(52) U.S. Cl. .................... 526/346; 526/335; 526/348.6; 524/10; 524/81

(58) Field of Classification Search ................. 526/346, 526/335, 348.6; 524/10, 81
See application file for complete search history.

(56) References Cited

FOREIGN PATENT DOCUMENTS

JP    2005-187338    *    7/2005

* cited by examiner

*Primary Examiner*—Ling-Siu Choi
(74) *Attorney, Agent, or Firm*—Rabin & Berdo, P.C.

(57) ABSTRACT

An eraser composition for de-flakes is disclosed. The composition comprises (i) a SEBS copolymer (styrene-ethylene-butylene-styrene) and SBS copolymer (styrene-butadiene-styrene) and TPE styrene, and the weight percentage being 10 to 35%; (ii) organic fillers of sodium carbonate, and pearl powder, and the weight percentage being about 30 to 60%; (iii) paraffin oil, and of a weight percentage of about 35 to 55%; (iv) palm oil, jojoba oil, linolein oil, moisturizer, deep cleanser, and olive oil, and a weight percentage of 5 to 15%; and (v) edible food pigments, or edible colorants, and the weight percentage of 0.1 to 0.5%.

1 Claim, No Drawings

ERASER COMPOSITION FOR DE-FLAKES

BACKGROUND OF THE INVENTION (a) Technical Field of the Invention

The present invention relates to a cosmetic composition, and in particular to an eraser composition for de-flakes formed on the human skin.

(b) Description of the Art

Complexion protection or cosmetics are available from the market or are introduced by cosmetic product promoters for cleansing and maintaining of the complexion.

Generally, complexion protection cosmetics are expensive and only effective to human complexion if it is used for a long period of time. To remove flakes or to remove spots on the skin, it is not only laborious but also expensive and time consuming. Further, prolong use of brushes, polishing devices, can easily damage the human complexion. Accordingly, it is an object of the present invention to provide an eraser composition which mitigates the above drawbacks. flakes, wherein the eraser composition promotes metabolism of cell of the skin.

SUMMARY OF THE INVENTION

The primary purpose of the present invention is to provide an eraser composition for de-flakes comprising (i) a SEBS copolymer (styrene-ethylene-butylene-styrene) and SBS copolymer (styrene-butadiene-styrene) and TPE ethane's rubber and other compositions, and the weight percentage being 10 to 35%; (ii) organic fillers of sodium carbonate, and pearl powder, and the weight percentage being about 30 to 60%; (iii) paraffin oil of weight percentage of about 35 to 55%; (iv) palm oil, jojoba oil, linolein oil, moisturizer, deep cleanser, olive oil and weight percentage of 5 to 15%; and (v) edible food pigments, edible colorants and the weight percentage of 0.1 to 0.5%.

Yet still another object of the present invention is to provide an eraser composition for de-flakes, wherein the fabrication process of the eraser composition is simple and the cost of fabrication is low.

Still another object of the present invention is to provide an eraser composition for de-flakes, wherein the eraser composition promotes metabolism of cell of the skin.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The present invention relates to an eraser composition for de-flakes comprising (i) a SEBS copolymer (styrene-ethylene-butylene-styrene) and SBS copolymer (styrene-butadiene-styrene) and TPE (thermoplastic elastomer) ethane's rubber (styrene) and other compositions, and the weight percentage being 10 to 35%; (ii) organic fillers of sodium carbonate, and pearl powder, and the weight percentage being about 30 to 60%; (iii) paraffin oil of weight percentage of about 35 to 55%; (iv) palm oil, jojoba oil, linolein oil, moisturizer, deep cleanser, and olive oil and weight percentage of 5 to 15%; and (v) edible food pigments or edible colorants and the weight percentage of 0.1 to 0.5%.

In accordance with the present invention, the above components (i) to (v) were mixed and evenly stirred. The products above were placed into a granulation machine and were squeezed into granules base material. The base material was transported into a molding or ejection molding machine. The material was thermal fused with a mold. Thus, a soft, elastic eraser was obtained to provide polishing for skin. This eraser provides the function of de-flakes, whitening, spots-diminishing, and prohibition of oil from the skin.

In accordance with the present invention, there is provided an eraser composition which is used for de-flakes, polishing, cleansing, etc.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An eraser composition for de-flakes comprising:
   (i) a SEBS copolymer (styrene-ethylene-butylene-styrene) and SBS copolymer (styrene-butadiene-styrene) and TPE (thermoplastic elastomer) ethylene rubber, and the weight percentage being 10 to 35%;
   (ii) organic fillers of sodium carbonate, and pearl powder, and the weight percentage being about 30 to 60%;
   (iii) paraffin oil, and the weight percentage of about 35 to 55%;
   (iv) palm oil, jojoba oil, linolein oil, moisturizer, deep cleanser, and olive oil, and the weight percentage of 5 to 15%; and
   (v) edible food pigments or edible colorants, and the weight percentage of 0.1 to 0.5%.

* * * * *